US011116713B2

(12) United States Patent
Rowland et al.

(10) Patent No.: US 11,116,713 B2
(45) Date of Patent: Sep. 14, 2021

(54) ORAL CARE COMPOSITIONS AND METHODS

(71) Applicant: BOARD OF TRUSTEES OF SOUTHERN ILLINOIS UNIVERSITY ON BEHALF OF SOUTHERN ILLINOIS, Edwardsville, IL (US)

(72) Inventors: Kevin Rowland, Pearland, TX (US); Brian Hearring, Sherman, IL (US)

(73) Assignee: The Board of Trustees of Southern Illinois University, Springfield, IL (US)

( * ) Notice: Subject to any disclaimer, the term of this patent is extended or adjusted under 35 U.S.C. 154(b) by 203 days.

(21) Appl. No.: 16/550,023

(22) Filed: Aug. 23, 2019

(65) Prior Publication Data

US 2020/0060953 A1 Feb. 27, 2020

Related U.S. Application Data

(60) Provisional application No. 62/722,328, filed on Aug. 24, 2018.

(51) Int. Cl.
*A61K 8/49* (2006.01)
*A61Q 11/00* (2006.01)
*A61K 8/43* (2006.01)

(52) U.S. Cl.
CPC ............ *A61K 8/498* (2013.01); *A61K 8/43* (2013.01); *A61Q 11/00* (2013.01)

(58) Field of Classification Search
None
See application file for complete search history.

(56) References Cited

U.S. PATENT DOCUMENTS

| | | |
|---|---|---|
| 5,204,089 A | 4/1993 | Hara et al. |
| 5,470,565 A | 11/1995 | Hayakawa et al. |
| 5,677,349 A | 10/1997 | Gilad et al. |
| 6,197,346 B1 | 3/2001 | Mathiowitz et al. |
| 7,544,816 B2 | 6/2009 | Chan et al. |
| 7,939,306 B2 | 5/2011 | Szeles et al. |
| 2007/0212311 A1 | 9/2007 | Burne et al. |
| 2017/0312329 A1* | 11/2017 | Cross, III ........... A61K 31/4172 |

FOREIGN PATENT DOCUMENTS

WO   2001/17494 A1   3/2001

OTHER PUBLICATIONS

Griswold, Ann R., et al., Regulation and Physiologic Significance of the Agmatine Deiminase System of *Streptococcus* Mutans UA159, Journal of Bacteriology, Feb. 2006, pp. 834-841, vol. 188, No. 3, American Society for Microbiology, Gainsville, Florida.
Griswold, AR, et al., Distribution, Regulation and Role of the Agmatine Deiminase System in Mutans Streptococci, University of Florida, Journal Compilation, Oral Microbiology Immunology 2009, 24: pp. 79-82, Gainsville, Florida, Printed in Singapore.
Ya-Ling Liu, et al., Progress Toward Understanding the Contribution of Alkali Generation in Dental Biofilms to Inhibition of Dental Caries, International Journal of Oral Science, Sep. 21, 2012, 4, pp. 135-140, www.nature.com/ijos, Gainsville, Florida.

* cited by examiner

*Primary Examiner* — Nannette Holloman
(74) *Attorney, Agent, or Firm* — Stinson LLP

(57) ABSTRACT

The present disclosure relates to compositions and methods for inhibiting the growth of, decreasing the amount of, and abolishing the growth of mutans streptococci.

20 Claims, 4 Drawing Sheets

ORAL CARE COMPOSITIONS AND METHODS

CROSS-REFERENCE TO RELATED APPLICATION

This application claims priority to U.S. Provisional Patent Application Ser. No. 62/722,328, filed Aug. 24, 2018, which is hereby incorporated by reference in its entirety.

FIELD OF THE INVENTION

The present disclosure relates to compositions and methods for inhibiting the growth of, reducing the amount of, or abolishing the growth of mutans streptococci in the oral cavity of a subject.

BACKGROUND

One of the most common global diseases is dental caries (cavities). It is estimated that industrialized countries spend up to 10% of their public health expenditures on periodontal disease, dental caries, and related dental care. The mutans group of streptococci, primarily serotypes of the *Streptococcus mutans* (*S. mutans*) species, are the chief etiologic agents of dental caries.

The metabolic pathway of *S. mutans* yields acid by-products that cause a drop in the pH of the oral cavity. To maintain a neutral intracellular pH, *S. mutans* generate an enzyme that actively pumps hydrogen ions out of the bacterium using agmatine as an energy source. The acidic environment created by metabolic processes of *S. mutans* in conjunction with the removal of intracellular hydrogen ions from the bacterium, allows *S. mutans* to survive while preventing growth of other beneficial microbes in the mouth.

The low pH levels generated by mutans streptococci lead to demineralization of tooth enamel, selection of acid-tolerant streptococci and can lead to dental caries. However, the use of broad-spectrum antimicrobials to combat mutans streptococci can decrease the beneficial bacterium in the mouth in addition to the mutans streptococci, and thus is not preferred. Further, current broad-spectrum antimicrobials can contribute to the spread of drug-resistant microorganisms, compromising the treatment of invasive infections including severe streptococcal infections. Many oral formulations contain high concentrations of alcohol for killing oral bacteria; however, for various reasons, alcohol in dental care compositions is not desirable.

Therefore, there is a need in the art for safe and effective reduced alcohol or alcohol-free oral care formulations that suppress the growth of mutans streptococci.

SUMMARY

One aspect of the present disclosure is directed to an oral care composition. An oral care composition of the invention comprises agmatine and EGCG in synergistic amounts effective to inhibit the growth of, reduce the amount of, or abolish the growth of mutans streptococci.

Other aspects of the present disclosure are directed to methods of inhibiting the growth of, reducing the amount of, or abolishing the growth of mutans streptococci. The methods comprise contacting mutans streptococci with an oral care composition of the invention.

Still other aspects of the present disclosure are directed to methods of treating caries in a subject. The methods comprise administering an oral care composition. The oral care composition comprises agmatine and EGCG in synergistic amounts effective to treat the caries in the subject.

Other aspects and iterations of the disclosure are described in more detail below.

DETAILED DESCRIPTION

Figure 1:
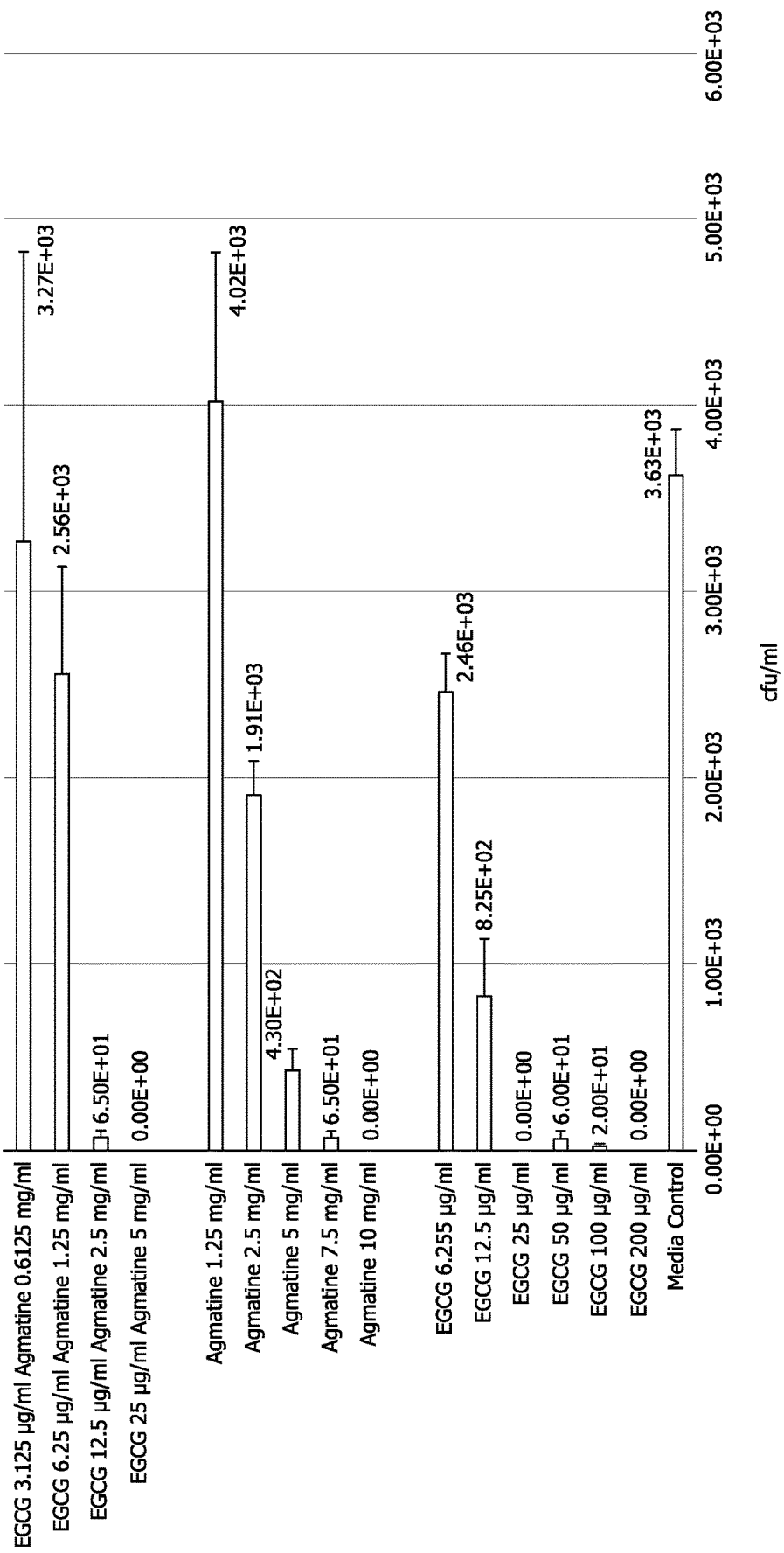
FIG. 1 depicts a graph showing the killing effect of EGCG, agmatine, or EGCG and agmatine in combination on *Streptococcus mutans* inoculum at $2.71 \times 10^4$ cfu/ml.
Figure 2:
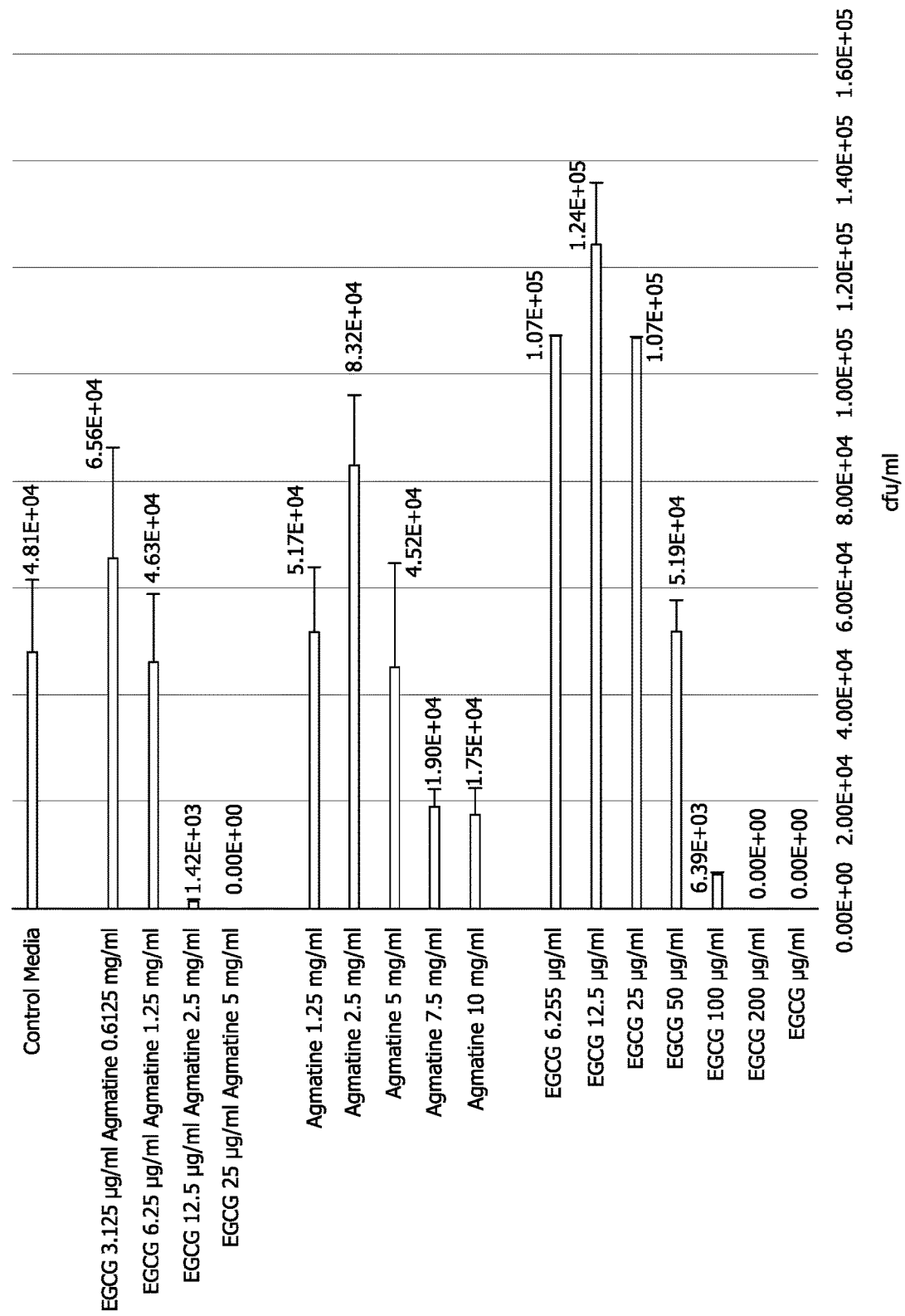
FIG. 2 depicts a graph showing the killing effect of EGCG, agmatine, or EGCG and agmatine in combination on *Streptococcus mutans* inoculum at $1.38 \times 10^6$ cfu/ml.
Figure 3:
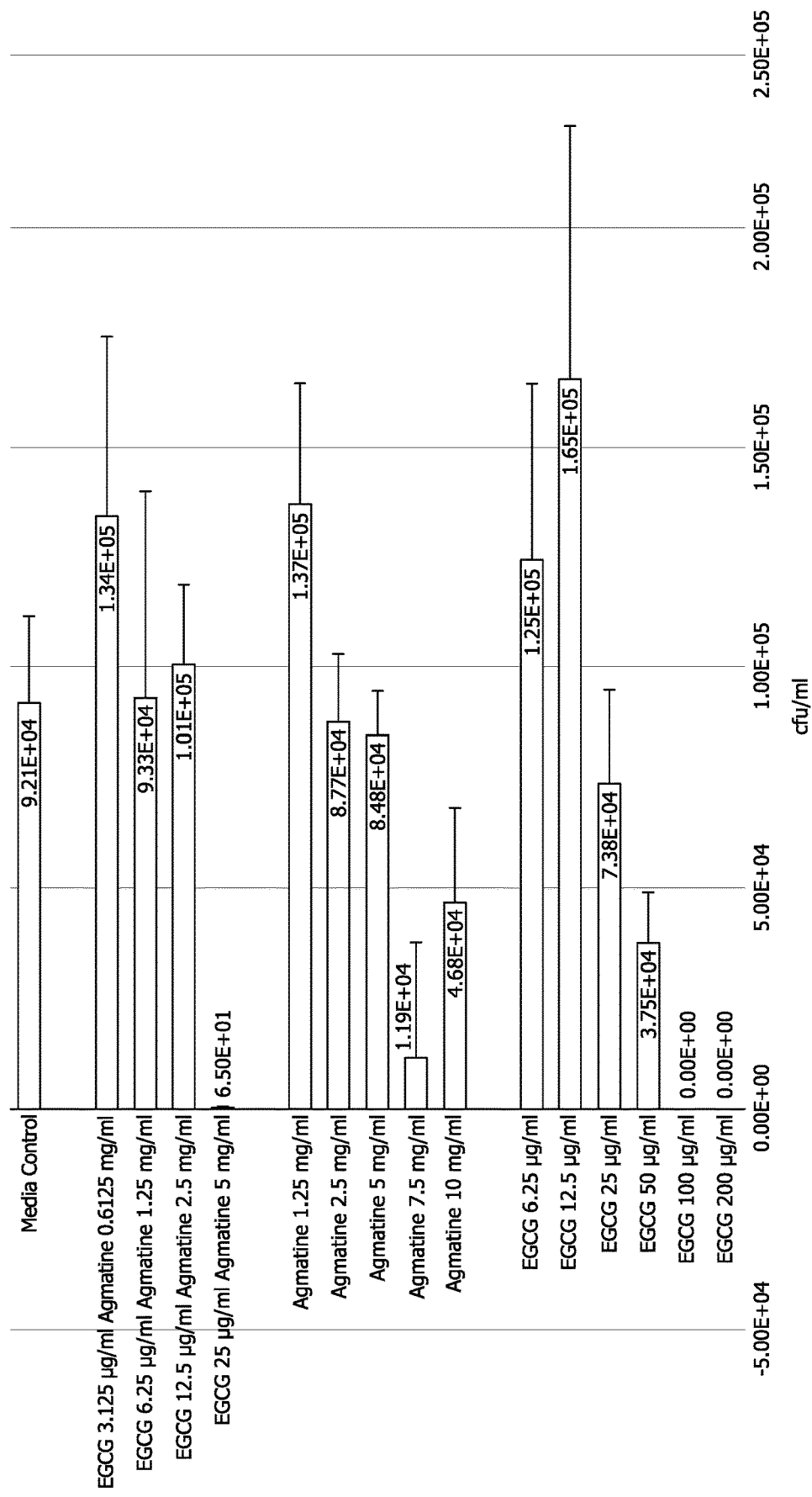
FIG. 3 depicts a graph showing the killing effect of EGCG, agmatine, or EGCG and agmatine in combination on *Streptococcus mutans* inoculum at $1.26 \times 10^5$ cfu/ml.

Provided herein are oral care compositions and methods for inhibiting the growth of, reducing the amount of, or abolishing the growth of mutans streptococci. Suitable compositions and methods of the invention are discussed in more detail below.

I. ORAL CARE COMPOSITIONS

An aspect of the present disclosure provides an oral care composition comprising isolated agmatine and isolated epigallocatechin gallate (EGCG). The concentrations of agmatine and EGCG that may be included in the oral care composition yield a synergistic antibacterial effect against mutans streptococci.

The term "oral care composition" is used herein to designate a product which in the ordinary course of usage is retained in the oral cavity for a time sufficient to contact substantially all of the dental and gingival surfaces, but which is not ingested. Non-limiting examples of oral care compositions may include dentifrices, toothpastes, tooth gels, dental creams, mouthwashes, mouth rinses, lozenges, mousses, foams, mouth sprays, oral tablets, dental implements, and chewing gum. In some aspects an oral care composition described herein inhibits the growth of, reduces the amount of, or abolishes the growth of mutans streptococci in the oral cavity. In other aspects an oral care composition described herein abolishes growth of mutans streptococci in the oral cavity. In certain aspects, an oral care composition reduces or prevents dental caries in the oral cavity.

Additionally, the term "oral care composition" may further designate a product which in the ordinary course of usage is retained in the oral cavity for a time sufficient to contact substantially all of the dental and gingival surfaces, but which is ingestable. Non-limiting examples of these oral care compositions may include a mint (such as a breath mint), chew, drink powder, concentrated drink mix, liquid drink, or tea.

(a) Agmatine

An oral care composition of the invention comprises purified or isolated agmatine. The term "agmatine" refers to a chemical substance naturally created from arginine through arginine decarboxylation, or a suitable salt thereof. Agmatine is also known as (4-aminobutyl)guanidine, and has the structure:

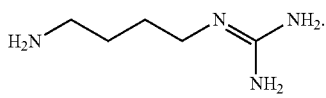

As used herein, the term agmatine can also encompass agmatine analogs, prodrugs or acceptable salts thereof. In some embodiments, agmatine may be isolated or purified from naturally occurring sources. In other embodiments, agmatine may be synthetically prepared by conventional techniques known in the art. Agmatine analogs may also be synthetically prepared by conventional synthesis, for instance, as disclosed by U.S. Pat. No. 5,677,349, the entire disclosure of which is hereby incorporated by reference. In an embodiment, acceptable salt forms of agmatine and agmatine analogs can be prepared by conventional techniques known in the art. In another embodiment, acceptable salt forms of agmatine and agmatine analogs may be purchased from commercial suppliers. By way of non-limiting example, a suitable agmatine salt may be agmatine sulfate.

In some embodiments, the amount of agmatine in the oral care composition of the invention can and will vary depending on the concentration of EGCG in the oral care composition of the invention. In some embodiments, the amount of agmatine in the oral care composition of the invention may be from about 0.5 mg/ml to about 20 mg/ml. In other embodiments, the amount of agmatine in the oral care composition of the invention may be at least about 0.5 mg/ml, at least about 1.0 mg/ml, at least about 5.0 mg/ml, at least about 10 mg/ml, at least about 15 mg/ml, or at least about 20 mg/ml. In additional embodiments, the amount of agmatine in the oral care composition of the invention may be at least about 0.3 mg/ml, at least about 0.4 mg/ml, at least about 0.5 mg/ml, at least about 0.6 mg/ml, at least about 0.7 mg/ml, at least about 1.0 mg/ml, at least about 1.25 mg/ml, at least about 1.5 mg/ml, at least about 2.0 mg/ml, at least about 2.5 mg/ml, at least about 3.0 mg/ml, at least about 3.5 mg/ml, at least about 4.0 mg/ml, at least about 4.5 mg/ml, at least about 5.0 mg/ml, at least about 5.5 mg/ml, at least about 6.0 mg/ml, at least about 6.5 mg/ml, at least about 7.0 mg/ml, at least about 7.5 mg/ml, at least about 8.0 mg/ml, or at least about 8.5 mg/ml. In some embodiments, the amount of agmatine in the oral care composition of the invention may be from about 0.500 mg/ml to about 0.525 mg/ml, from about 0.525 mg/ml to about 0.550 mg/ml, from about 0.550 mg/ml to about 0.575 mg/ml, from about 0.575 mg/ml to about 0.600 mg/ml, from about 0.600 mg/ml to about 0.625 mg/ml, from about 0.625 mg/ml to about 0.650 mg/ml, from about 0.650 mg/ml to about 0.675 mg/ml, or from about 0.675 mg/ml to about 0.700 mg/ml.

(b) Epigallocatechin Gallate (EGCG)

The term "EGCG" refers to an ester of epigallocatechin and gallic acid (i.e., epigallocatechin gallate). As used herein, "EGCG" also encompasses the term "epigallocatechin-3-gallate," which is another term known in the art to describe an ester of epigallocatechin and gallic acid.

In general, the oral care composition of the invention comprises EGCG. In an embodiment, the oral care composition of the invention comprises EGCG, EGCG analogs, prodrugs, or acceptable salts thereof. In another embodiment, EGCG may be isolated or purified from naturally occurring sources using methods known in the art. Non limiting examples of naturally occurring sources include green tea, white teas, black tea, apple skin, plums, onions, hazelnuts, pecans, and carob powder. In another embodiment, EGCG may be synthetically prepared by conventional techniques known in the art. In another embodiment, synthetic EGCG analogs can be prepared by conventional synthesis as disclosed by U.S. Pat. No. 7,544,816 the entire disclosure of which is hereby incorporated by reference. In an embodiment, acceptable salt forms of EGCG and EGCG analogs can be prepared by conventional techniques known in the art. Acceptable salt forms of EGCG and EGCG analogs include, but are not limited to, the following: inorganic acid addition salts such as hydrochloride, hydrobromide, sulfate, phosphate, and nitrate; organic acid addition salts such as acetate, galactarate, propionate, succinate, lactate, glycolate, malate, tartrate, citrate, maleate, fumarate, methanesulfonate, salicylate, p-toluenesulfonate, benzenesulfonate, and ascorbate; salts with acidic amino acids such as aspartate and glutamate. The salts may be in some cases hydrates or solvates with alcohols and other solvents.

In some embodiments, the amount of EGCG in the oral care composition of the invention can and will vary depending on the concentration of agmatine in the oral care composition of the invention. In some embodiments, the amount of EGCG in the oral care composition of the invention may be from about 2 µg/ml to about 250 µg/ml. In other embodiments, the amount of EGCG in the oral care composition of the invention may be at least about 2 µg/ml, at least about 4 µg/ml, at least about 6 µg/ml, at least about 12 µg/ml, at least about 25 µg/ml, at least about 50 µg/ml, at least about 100 µg/ml, at least about 150 µg/ml, or at least about 200 µg/ml. In additional embodiments, the amount of EGCG in the oral care composition of the invention may be at least about 2 µg/ml, at least about 3 µg/ml, at least about 4 µg/ml, at least about 5 µg/ml, at least about 6 µg/ml, at least about 7 µg/ml, at least about 8 µg/ml, at least about 9 µg/ml, at least about 10 µg/ml, at least about 11 µg/ml, at least about 12 µg/ml, at least about 13 µg/ml, at least about 14 µg/ml, at least about 15 µg/ml, at least about 16 µg/ml, at least about 17 µg/ml, at least about 18 µg/ml, at least about 19 µg/ml, at least about 20 µg/ml, at least about 21 µg/ml, at least about 22 µg/ml, at least about 23 µg/ml, at least about 24 µg/ml, at least about 25 µg/ml, or at least about 26 µg/ml. In additional embodiments, the amount of EGCG in the oral care composition of the invention may be from about 3.00 µg/ml to about 3.25 µg/ml, from about 3.25 µg/ml to about 3.50 µg/ml, from about 3.50 µg/ml to about 3.75 µg/ml, from about 3.75 µg/ml to about 4.00 µg/ml, from about 4.00 µg/ml to about 4.25 µg/ml, from about 4.25 µg/ml to about 4.50 µg/ml, from about 4.50 µg/ml to about 4.75 µg/ml, from about 4.75 µg/ml to about 5.00 µg/ml, from about 5.00 µg/ml to about 5.25 µg/ml, from about 5.25 µg/ml to about 5.50 µg/ml, from about 5.50 µg/ml to about 5.75 µg/ml, from about 5.75 µg/ml to about 6.00 µg/ml, from about 6.00 µg/ml to about 6.25 µg/ml, from about 6.25 µg/ml to about 6.50 µg/ml, from about 6.50 µg/ml to about 6.75 µg/ml, from about 6.75 µg/ml to about 7.00 µg/ml, from about 7.00 µg/ml to about 7.25 µg/ml, from about 7.25 µg/ml to about 7.50 µg/ml, from about 7.50 µg/ml to about 7.75 µg/ml, from about 7.75 µg/ml to about 8.00 µg/ml, from about 8.00 µg/ml to about 8.25 µg/ml, from about 8.25 µg/ml to about 8.50 µg/ml, from about 8.50 µg/ml to about 8.75 µg/ml, from about 8.75 µg/ml to about 9.00 µg/ml, from about 9.00 µg/ml to about 9.25 µg/ml, from about 9.25 µg/ml to about 9.50 µg/ml, from about 9.50 µg/ml to about 9.75 µg/ml, from about 9.75 µg/ml to about 10.00 µg/ml, from about 10.00 µg/ml to about 10.25 µg/ml, from about 10.25 µg/ml to about 10.50 µg/ml, from about 10.50 µg/ml to about 10.75 µg/ml, from about 10.75 µg/ml to about 11.00 µg/ml, from about 11.00 µg/ml to about 11.25 µg/ml, from about 11.25 µg/ml to about 11.50 µg/ml, from about 11.50 µg/ml to about 11.75

µg/ml, from about 11.75 µg/ml to about 12.00 µg/ml, from about 12.00 µg/ml to about 12.25 µg/ml, from about 12.25 µg/ml to about 12.50 µg/ml, from about 12.50 µg/ml to about 12.75 µg/ml, from about 12.75 µg/ml to about 13.00 µg/ml, from about 13.00 µg/ml to about 13.25 µg/ml, from about 13.25 µg/ml to about 13.50 µg/ml, from about 13.50 µg/ml to about 13.75 µg/ml, or from about 13.75 µg/ml to about 14.00 µg/ml.

(c) Mutans Streptococci

The term "mutans streptococci" collectively refers to the species comprising the mutans group of streptococci. The mutans group of streptococci consists of seven species that can be classified into eight serotypes: *Streptococcus mutans* (serotypes c, e and f), *Streptococcus sobrinus* (serotypes d and g), *Streptococcus criceti* (serotype a), *Streptococcus downei* (serotype h), *Streptococcus ferus* (serotype c), *Streptococcus macacae* (serotype c) and *Streptococcus ratti* (serotype b).

In general, an oral care composition of the invention contacts mutans streptococci. In an embodiment, the oral care composition of the invention contacts at least one of the serotypes classified in the mutans group of streptococci, at least one of the species comprising the mutans group of streptococci, a combination of serotypes classified in the mutans group of streptococci, a combination of the species comprising the mutans group of streptococci, or a combination of any serotype(s) or species of the mutans group of streptococci. In another embodiment, an oral care composition of the invention contacts *S. mutans* and/or *S. sobrinus*. In yet another embodiment, the oral care composition of the invention contacts *S. sobrinus*. In another embodiment, the oral care composition of the invention contacts serotype d *S. sobrinus*, serotype g *S. sobrinus*, or serotypes d and g *S. sobrinus*. In an embodiment, the oral care composition of the invention contacts *S. mutans*. In another embodiment, the oral care composition of the invention contacts serotype c *S. mutans*, serotype e *S. mutans*, serotype f *S. mutans*, or any combination thereof. For example, in one embodiment, the oral care composition of the invention contacts serotypes c, e, and f *S. mutans*.

In some embodiments, the amount of colony forming units (cfu) of mutans streptococci that contact the oral care composition of the invention can and will vary depending on certain variables. Non limiting examples of such variables include, the serotype(s) comprising the colony of mutans streptococci, the strain(s) comprising the colony of mutans streptococci, the growth rate of colony of mutans streptococci, and the environment sustaining the colony of mutans streptococci, including factors such as the tonicity, pH, temperature, and other environmental factors known to impact the colony of mutans streptococci. In some embodiments, the amount of colony forming units (cfu) of mutans streptococci that contact the oral care composition of the invention may be from $1\times10^4$ cfu/ml to $1\times10^7$ cfu/ml. In other embodiments, the amount of colony forming units (cfu) of mutans streptococci that contact the oral care composition of the invention may be at least about $1\times10^4$ cfu/ml, at least about $5\times10^4$ cfu/ml, at least about $1\times10^5$ cfu/ml, at least about $5\times10^5$ cfu/ml, at least about $1\times10^6$ cfu/ml, at least about $5\times10^5$ cfu/ml, or at least about $1\times10^7$ cfu/ml. In additional embodiments, the amount of colony forming units (cfu) of mutans streptococci that contact the oral care composition of the invention may be at least about $2.0\times10^4$ cfu/ml, at least about $2.3\times10^4$ cfu/ml, at least about $2.5\times10^4$ cfu/ml, at least about $2.7\times10^4$ cfu/ml, at least about $2.9\times10^4$ cfu/ml, at least about $3.0\times10^4$ cfu/ml, at least about $2.3\times10^4$ cfu/ml, at least about $1.0\times10^5$ cfu/ml, at least about $1.1\times10^5$ cfu/ml, at least about $1.2\times10^5$ cfu/ml, at least about $1.3\times10^5$ cfu/ml, at least about $1.4\times10^5$ cfu/ml, at least about $1.0\times10^6$ cfu/ml, at least about $1.1\times10^6$ cfu/ml, at least about $1.2\times10^6$ cfu/ml, at least about $1.3\times10^6$ cfu/ml, at least about $1.4\times10^6$ cfu/ml, at least about $1.5\times10^6$ cfu/ml, at least about $5.0\times10^6$ cfu/ml, at least about $5.1\times10^6$ cfu/ml, at least about $5.2\times10^6$ cfu/ml, at least about $5.3\times10^6$ cfu/ml, or at least about $5.4\times10^6$ cfu/ml.

(d) Synergistic Compound Combinations

As used herein, a combinatorial treatment comprised of two compounds is "synergistic" if the effect of the combination is greater than the sum of the effects of two compounds acting individually. A synergistic compound combination may be beneficial for treating bacterium at a greater efficacy with lower-dose combinations and may decrease the occurrence of resistance mechanisms known to develop in bacterium treated with higher-dose monotherapies or non-synergistic combinatorial treatments.

In an embodiment, an oral care composition of the invention comprises agmatine and EGCG in synergistic amounts effective to inhibit the growth of mutans streptococci. In some embodiments, the oral care composition of the invention comprising agmatine and EGCG in synergistic amounts effective to inhibit the growth of mutans streptococci can and will vary in the amount of agmatine and EGCG depending on certain variables. Non limiting examples of such variables may include, the serotype(s) comprising the colony of mutans streptococci, the strain(s) comprising the colony of mutans streptococci, the growth rate of the colony of mutans streptococci, and the environment sustaining the colony of mutans streptococci, including factors such as the tonicity, pH, temperature, and other environmental factors known to impact the colony of mutans streptococci. In some embodiments, the amount of agmatine and EGCG may be from about 0.6 mg/ml and about 3.0 µg/ml, respectively, to about 5 mg/ml and about 25 µg/ml, respectively. In other embodiments, the amount of agmatine and EGCG may be at least about 0.6 mg/ml and 3.0 µg/ml, respectively, at least about 1.3 mg/ml and 6.3 µg/ml, respectively, at least about 2.5 mg/ml and 12.5 µg/ml, respectively, or at least about 5.0 mg/ml and 25 µg/ml, respectively. In other embodiments, the amount of agmatine and EGCG may be at least about 0.6125 mg/ml and 3.125 µg/ml, respectively, or at least about 1.25 mg/ml and 6.25 µg/ml, respectively.

In an embodiment, the oral care composition of the invention comprises agmatine and EGCG in synergistic amounts effective to reduce the amount of mutans streptococci. In some embodiments, the oral care composition of the invention comprising agmatine and EGCG in synergistic amounts effective to reduce the amount of mutans streptococci can and will vary in the amount of agmatine and EGCG depending on certain variables. Non limiting examples of such variables include, the serotype(s) comprising the colony of mutans streptococci, the strain(s) comprising the colony of mutans streptococci, the growth rate of the colony of mutans streptococci, and the environment sustaining the colony of mutans streptococci, including factors such as the tonicity, pH, temperature, and other environmental factors known to impact the colony of mutans streptococci. In some embodiments, the amount of agmatine and EGCG may be from about 0.6 mg/ml and about 3.0 µg/ml, respectively, to about 5 mg/ml and about 25 µg/ml, respectively. In other embodiments, the amount of agmatine and EGCG may be at least about 0.6 mg/ml and about 3.0 µg/ml, respectively, at least about 1.3 mg/ml and about 6.3 µg/ml, respectively, at least about 2.5 mg/ml and about 12.5 µg/ml, respectively, or at least about 5.0 mg/ml and about 25

μg/ml, respectively. In other embodiments, the amount of agmatine and EGCG may be at least about 0.6125 mg/ml and about 3.125 μg/ml, respectively, or at least about 1.25 mg/ml and about 6.25 μg/ml, respectively.

In an embodiment, the oral care composition of the invention comprises agmatine and EGCG in synergistic amounts effective to abolish the growth of mutans streptococci. In some embodiments, the oral care composition of the invention comprising agmatine and EGCG in synergistic amounts effective to abolish the growth of mutans streptococci can and will vary in the amount of agmatine and EGCG depending on certain variables. Non limiting examples of such variables include, the serotype(s) comprising the colony of mutans streptococci, the strain(s) comprising the colony of mutans streptococci, the growth rate of the colony of mutans streptococci, and the environment sustaining the colony of mutans streptococci, including factors such as the tonicity, pH, temperature, and other environmental factors known to impact the colony of mutans streptococci. In some embodiments, the amount of agmatine and EGCG may be from about 0.6 mg/ml and about 3.0 μg/ml, respectively, to about 5 mg/ml and about 25 μg/ml, respectively. In other embodiments, the amount of agmatine and EGCG may be at least about 0.6 mg/ml and about 3.0 μg/ml, respectively, at least about 1.3 mg/ml and about 6.3 μg/ml, respectively, at least about 2.5 mg/ml and about 12.5 μg/ml, respectively, or at least about 5.0 mg/ml and about 25 μg/ml, respectively. In other embodiments, the amount of agmatine and EGCG may be at least about 0.6125 mg/ml and about 3.125 μg/ml, respectively, or at least about 1.25 mg/ml and about 6.25 μg/ml, respectively.

(e) Formulations

In an embodiment, an oral care composition of the invention comprises a therapeutically effective amount of isolated agmatine and isolated EGCG, along with suitable, pharmaceutically-acceptable excipient(s) for administration to a subject. In some embodiments, oral care compositions described herein have low alcohol content, e.g. less than 25%. In preferred embodiments, oral care compositions described herein are essentially free of alcohol.

In an embodiment, the pharmaceutically-acceptable excipient(s) may include the usual and conventional components of dentifrices, toothpastes (including gels and gels for subgingival application), mouthwashes, mouthrinses, mouth sprays, creams, mousses, foams, oral tablets, chewing gums, and lozenges (including breath mints). The oral care composition of the invention may include conventional components for a pharmaceutically acceptable carrier. Conventional components suitable for the formulations of oral care compositions are well known in the art. Conventional components may include, but are not limited to, an additional antimicrobial agent (different from agmatine and EGCG), an anti-plaque agent, a tooth whitening or tooth bleaching composition, a flavorant, a sweetening agent, an adhesion agent, a surfactant, a foam modulator, an abrasive, a humectant, a mouth feel agent, a colorant, a tartar control (anticalculus) agent, a fluoride ion source, a saliva stimulating agent, a thickening agent, an anti-sensitivity agent, an antioxidant, a nutrient, an enzyme, a propellant, a binder, a diluent (filler), a disintegrant, a preservative, a lubricant, a dispersant, a pH modifier, a chelating agent, a release-controlling polymer, and combinations thereof. It is understood that while general attributes of each of the above categories of materials may differ, there may be some common attributes, and any given material may serve multiple purposes within two or more of such categories of materials. Selection of conventional components to include in oral care compositions can and will vary depending on the dosage form of the oral care composition and compatibility with other ingredients of the oral care composition. Further, selection of conventional components to include in oral care compositions of the invention can and will vary depending on secondary considerations, including but not limited to, taste, cost, and shelf stability.

(i) Antimicrobial Agents

An additional antimicrobial agent may be included to minimize the degradation of an oral care composition by microbial agents, including, without limitation, bacteria and fungi. An antimicrobial agent may be included to minimize, inhibit, and/or degrade a biofilm in the oral cavity. Antimicrobial agents may include, without limit, triclosan, cetyl pyridinium chloride, magnolia extract, magnolol, honokiol, butyl magnolol, propyl honokiol, zinc chloride, zinc lactate, zinc citrate, stannous fluoride, stannous chloride, parabens, chlorobutanol, phenol, calcium propionate, sodium nitrate, sodium nitrite, $Na_2EDTA$, and sulfites including, without limit, sulfur dioxide, sodium bisulfite, and potassium hydrogen sulfite. An additional antimicrobial agent may be optionally present in a total amount of from about 0.01 wt % to about 15 wt %, for example from about 0.05 wt % to about 2 wt %, from about 0.1 wt % to about 2.5 wt %, or from about 0.1 wt % to about 0.5 wt %.

(ii) Anti-Plaque Agents

An anti-plaque agent may be included to prevent, inhibit, eliminate or decrease growth of bacterial plaque formation without affecting the biological equilibrium within the oral cavity. Any orally acceptable chemical that prevents, inhibits, or decreases growth of bacterial plaque formation to sufficiently benefit gingivitis and/or caries may be used. Examples of anti-plaque agents may include, but are not limited to, enzymes (e.g., protease, lipase, nuclease, dextranase, mucinase, mutanase, glucoseoxidase, amyloglucosidase), bisbiguanides (e.g., chlorhexidine, alexidene, octenidine), quaternary ammonium compounds (e.g., cetyl pyridinium chloride, benzalconium chloride), surfactants (e.g., sodium lauryl sulphate, delmopinol, hexetidine), metal salts (e.g., zinc, tin (stannous fluoride), copper), essential oils (e.g., thymol, eucalyptol, methyl salicylate, menthol), phenolic compunds (e.g., thymol, 4-hexylresorcinol, 2-phenylphenol eucalyptol, listerene), natural products and extracts (e.g., sanguinarine, apigenin, tt-farnesol), iodine, povidone iodine, chloramine-t sodium hypochlorite, triclosan, salifluor, xylitol, ammonium fluoride, chlorothymol, and urea peroxide, chlorhexidine, oftriclosan, or combinations thereof. An anti-plaque agent may be optionally present in a total amount of from about 0.01 wt % to about 15 wt %, for example from about 0.05 wt % to about 2 wt %, from about 0.1 wt % to about 2.5 wt %, or from about 0.1 wt % to about 0.5 wt %.

(iii) Tooth Whitening or Tooth Bleaching Compositions

An oral care composition of the invention may also include a tooth whitening or tooth bleaching composition. Suitable tooth whitening or tooth bleaching compositions are known in the art, and may include peroxides, metal chlorites, and/or persulfates. Peroxides may include hydroperoxides, hydrogen peroxide, peroxides of alkali and alkaline earth metals, organic peroxy compounds, peroxy acids, and mixtures thereof. Peroxides of alkali and alkaline earth metals may include lithium peroxide, potassium peroxide, sodium peroxide, magnesium peroxide, calcium peroxide, barium peroxide, and mixtures thereof. Other peroxides may include perborate, urea peroxide, and mixtures thereof. Suitable metal chlorites may include calcium chlorite, barium chlorite, magnesium chlorite, lithium chlorite, sodium chlorite, and potassium chlorite. Such compositions may be added in effective amounts, e.g., from about 1 wt % to about 20 wt % by weight based on the total weight of the oral care composition, depending on the agent chosen.

(iv) Flavorants

Flavorants among those useful herein include any material or mixture of materials operable to enhance the taste of the oral care composition. Any orally acceptable natural or synthetic flavorant may be used, such as flavoring oils, flavoring aldehydes, esters, alcohols, similar materials, and combinations thereof. Flavorants may include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients may include menthol, menthyl acetate, menthyl lactate, camphor, eucalyptus oil, eucalyptol, anethole, eugenol, cassia, oxanone, [alpha]-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof. One or more flavorants may be optionally present in a total amount of from about 0.01 wt % to about 15 wt %, for example, from about 0.05 wt % to about 2 wt %, from about 0.1 wt % to about 2.5 wt %, or from about 0.1 wt % to about 0.5 wt %.

(v) Sweetening Agents

Sweetening agents among those useful herein may include dextrose, polydextrose, sucrose, maltose, dextrin, dried invert sugar, mannose, xylose, ribose, fructose, levulose, galactose, corn syrup, partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof. A sweetening agent may be optionally present in a total amount of from about 0.01 wt % to about 15 wt %, for example from about 0.05 wt % to about 2 wt %, from about 0.1 wt % to about 2.5 wt %, or from about 0.1 wt % to about 0.5 wt %.

(vi) Adhesion Agents

Depending upon the formulation, it may be desirable to include an adhesion agent. Examples of adhesion agents include, but are not limited to, polyvinyl pyrrolidone (PVP), PVP-vinyl acetate copolymers, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, carboxymethylcellulose, carboxypropylcellulose, cellulosic ethers, polysaccharide gums, proteins, and the like. An adhesion agent may be optionally present in a total amount of from about 0.01 wt % to about 15 wt %, for example from about 0.05 wt % to about 2 wt %, from about 0.1 wt % to about 2.5 wt %, or from about 0.1 wt % to about 0.5 wt %.

(vii) Surfactants

An oral care composition of the invention may comprise one or more surface active agents (surfactants) as needed. These surfactants may be of the anionic, nonionic, cationic or amphoteric type. Suitable surfactants may include, without limitation, water-soluble salts of $C_{8-20}$ alkyl sulfates, sulfonated monoglycerides of $C_{8-20}$ fatty acids, sarcosinates, taurates, sodium lauryl sulfate, sodium dodecylbenzene sulfonate, sodium cocoyl monoglyceride sulfonate, sodium lauryl sarcosinate, sodium lauryl isoethionate, sodium laureth carboxylate, sodium dodecyl benzenesulfonate, and cocoamidopropyl betaine, block polymers of polyoxyethylene and polyoxypropylene, N-methyl-N-palm itoyl tauride, sodium-N-lauroyl sarcosinate, other sarcosinates, and sulfosuccinates, or the like.

(viii) Foam Modulators

Depending upon the formulation, it may be desirable to include a foam modulator or combination thereof. Foam modulators useful herein include materials operable to increase amount, thickness, or stability of foam generated by the composition (e.g., dentifrice or polish compositions) upon agitation. Any orally acceptable foam modulator can be used, including polyethylene glycols (PEGs), also known as polyoxyethylenes. High molecular weight PEGs are suitable, including those having an average molecular weight of from about 200,000 to about 7,000,000, for example from about 500,000 to about 5,000,000 or from about 1,000,000 to about 2,500,000. One or more PEGs are optionally present in a total amount of from about 0.1 wt % to about 10 wt %, for example from about 0.2 wt % to about 5 wt % or from about 0.25 wt % to about 2 wt %.

(ix) Abrasives

An oral care composition of the invention may further comprise an optional abrasive useful, for example, as a polishing agent. When abrasives are present, the average particle size is generally from about 0.1 to about 30 microns, for example, from about 1 to about 20 microns or from about 5 to 15 microns.

Any orally acceptable abrasive may be used, but type, fineness, (particle size) and amount of abrasive should be selected so that tooth enamel is not excessively abraded in normal use of the oral care composition. Suitable optional abrasives include silica, for example in the form of precipitated silica or as admixed with alumina, insoluble phosphates, calcium carbonate, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate. Some embodiments provide oral care compositions comprising from about 0 wt % to about 15 wt % abrasive based on the total weight of the oral care composition.

(x) Humectants

An oral care composition may comprise a humectant. A humectant may serve to keep paste compositions from hardening upon exposure to air, to give compositions a moist feel to the mouth, and, for particular humectants, to impart desirable sweetness of flavor to oral care compositions. Non-limiting examples of humectants for use in oral care compositions of the invention may include edible polyhydric alcohols such as glycerin, sorbitol, xylitol, butylene glycol, polyethylene glycol, and propylene glycol, especially sorbitol and glycerin. In some embodiments, a humectant, on a pure humectant basis, generally comprises from about 0 wt % to about 70 wt %, preferably from about 5 wt % to about 25 wt % of the oral care compositions described herein.

(xi) Mouth Feel Agents

An oral care composition of the invention may comprise one or more mouth feel agents to affect the mouth feel of the oral care composition. Mouth-feel agents encompass materials imparting a desirable texture or other feeling during use of the oral care composition. A mouth feel agent may be optionally present in a total amount of from about 0.01 wt % to about 15 wt %, for example from about 0.05 wt % to about 2 wt %, from about 0.1 wt % to about 2.5 wt %, or from about 0.1 wt % to about 0.5 wt %.

(xii) Colorants

Depending upon the formulation, it may be desirable to include a colorant. Suitable colorants may include, without limitation, food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in various embodiments. Colorants among those useful herein may include pigments, dyes, flakes and agents imparting a particular luster or reflectivity such as pearling agents. In various embodiments, colorants are operable to provide a white or light-colored coating on a dental surface, to act as an indicator of locations on a dental surface that have been effectively contacted by the oral care composition, and/or to modify appearance, in particular color and/or opacity, of the oral care composition to enhance attractiveness to the consumer. Any orally acceptable colorant may be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of from about 0.001 wt % to about 20 wt %, for example from about 0.01 wt % to about 10 wt % or from about 0.1 wt % to about 5 wt %.

(xiii) Tartar Control (anticalculus) Agents

The oral care compositions of the invention optionally comprise a tartar control (anticalculus) agent. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof. Other useful tartar control agents include polycarboxylate polymers and polyvinyl methyl ether/maleic anhydride (PVM/MA) copolymers, such as GANTREZ®. An tartar control (anticalculus) agent may be optionally present in a total amount of from about 0.01 wt % to about 15 wt %, for example from about 0.05 wt % to about 2 wt %, from about 0.1 wt % to about 2.5 wt %, or from about 0.1 wt % to about 0.5 wt %.

(xiv) Fluoride Ion Source

Fluoride salts and fluoride ion sources, e.g., fluoride salts which may be soluble, are known in the art and may be incorporated into the oral care compositions of the invention. Representative fluoride ion sources include, but are not limited to: stannous fluoride, sodium fluoride, potassium fluoride, potassium monofluorophosphate, sodium monofluorophosphate, ammonium monofluorophosphate, sodium fluorosilicate, ammonium fluorosilicate, amine fluoride such as olaflur (N'-octadecyltrimethylendiamine-N,N,N'-tris(2-ethanol)-dihydrofluoride), ammonium fluoride, and combinations thereof. In certain embodiments the fluoride ion source includes stannous fluoride, sodium fluoride, amine fluorides, sodium monofluorophosphate, as well as mixtures thereof. Preferably, the fluoride salt is sodium fluoride. In certain embodiments, the oral care composition of the invention may also contain a source of fluoride ions or fluorine-providing ingredient in amounts sufficient to supply from about 50 to about 5000 ppm fluoride ion, e.g., from about 100 to about 1000, from about 200 to about 500, or about 250 ppm fluoride ion. Fluoride ion sources may be added to the oral care compositions of the invention at a concentration of from about 0.001 wt % to about 10 wt %, for example from about 0.003 wt % to about 5 wt %, from about 0.01 wt % to about 1 wt %, or from about 0.01 wt % to about 0.05 wt %. However, it is to be understood that the weights of fluoride salts to provide the appropriate level of fluoride ion will vary based on the weight of the counter ion in the salt, and one of skill in the art will be able to readily determine such amounts.

(xv) Saliva Stimulating Agent

The oral care compositions of the invention may optionally comprise a saliva stimulating agent useful, for example, in amelioration of dry mouth. Any orally acceptable saliva stimulating agent may be used, as long as the saliva stimulating agent doesn't impede the ability of the oral care composition to inhibit mutans streptococci. A saliva stimulating agent may be optionally present in a total amount of from about 0.01 wt % to about 15 wt %, for example from about 0.05 wt % to about 2 wt %, from about 0.1 wt % to about 2.5 wt %, or from about 0.1 wt % to about 0.5 wt %.

(xvi) Thickening Agents

An oral care composition of the invention may comprise a thickening agent. Suitable thickening agents may include, without limitation, carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth may also be used. Colloidal magnesium aluminum silicate or finely divided silica may be used as part of the thickening agent to further improve texture. In some embodiments, a class of thickening or gelling agents includes a class of homopolymers of acrylic acid crosslinked with an alkyl ether of pentaerythritol or an alkyl ether of sucrose, or carbomers. Carbomers are commercially available from B. F. Goodrich as the Carbopol® series. Particularly preferred carbopols include Carbopol 934, 940, 941, 956, and mixtures thereof.

Thickening agents may be included in an amount of from about 0.1 wt % to about 35 wt %, preferably from about 2 wt % to about 25 wt %, more preferably from about 4 wt % to about 15 wt % based on the total oral care composition. Higher concentrations may be used, if suitable, for chewing gums, lozenges (including breath mints), sachets, non-abrasive gels and subgingival gels. The skilled person will readily understand the appropriate concentration for thickening agents in a given formulation.

(xvii) Antisensitivity Agents

An oral care composition of the invention may optionally incorporate one or more antisensitivity agents. The oral care compositions of the invention may also be used to treat hypersensitivity by blocking dentin tubules when applied to a tooth, which can be accomplished by incorporating an antisensitivity agent. Antisensitivity agents include, as an example, potassium salts such as potassium nitrate, potassium bicarbonate, potassium chloride, potassium citrate, and potassium oxalate; capsaicin; eugenol; strontium salts; zinc salts; chloride salts and combinations thereof. Such agents may be added in effective amounts, for example, from about 1 wt % to about 20 wt % based on the total weight of the oral care composition. The skilled person will understand that the concentration depends in part on the agent chosen.

(xviii) Antioxidants

In some embodiments, an oral care composition of the invention may further comprise an antioxidant. Any orally acceptable antioxidant may be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof. An antioxidant may be optionally present in a total amount of from about 0.01 wt % to about 15 wt %, for example from about 0.05 wt % to about 2 wt %, from about 0.1 wt % to about 2.5 wt %, or from about 0.1 wt % to about 0.5 wt %.

(xix) Nutrients

In some embodiments, an oral care composition of the invention may further comprise a nutrient. Suitable nutrients include vitamins, minerals, amino acids, and mixtures thereof. Vitamins may include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutrients may include amino acids (such as L-tryptophan, L-lysine, methionine, threonine, levocarnitine and L-carnitine), lipotropics (such as choline, inositol, betaine, and linoleic acid), and mixtures thereof. A nutrient may be optionally present in a total amount of from about 0.01 wt % to about 15 wt %, for example from about 0.05 wt % to about 2 wt %, from about 0.1 wt % to about 2.5 wt %, or from about 0.1 wt % to about 0.5 wt %.

(xxi) Enzymes

In some embodiments, an oral care composition of the invention may comprise an enzyme. Non-limiting examples of enzymes useful in the practice of the present invention may be as described in U.S. Pat. No. 7,939,306 which is incorporated herein by reference. For instance, enzymes useful in the practice of the present invention may include papain, bromelain, chymotrypsin, ficin, alcalase, alpha-amylase, beta-amylase, dextranase, plant lipase, gastric lipase, pancreatic lipase, pectinase, tannase lysozyme, serine protease, and pectinase. An enzyme may be optionally present in a total amount of from about 0.01 wt % to about 15 wt %, for example from about 0.05 wt % to about 2 wt %, from about 0.1 wt % to about 2.5 wt %, or from about 0.1 wt % to about 0.5 wt %.

(xxii) Propellants

In some embodiments, an oral care composition described herein may comprise one or more propellants known in the art. The selection of propellant(s) can and will vary depending on various factors such as the desired rate of increase in foam volume, environmental standards and/or consumer safety issues. Non-limiting examples of propellants may include compressed air, nitrous oxide, and carbon dioxide and, a volatile hydrocarbon or mixture of volatile hydrocarbons having a vapor pressure of 10 to 90 pounds per sq. inch at about 20° C.

(xxiii) Binders

An oral care composition of the invention may include a binder. Non-limiting examples of suitable binders may include starches, pregelatinized starches, gelatin, polyvinylpyrrolidone, cellulose, methylcellulose, sodium carboxymethylcellulose, ethylcellulose, polyacrylamides, polyvinyloxazolidone, polyvinylalcohols, $C_{12}$-$C_{18}$ fatty acid alcohols, polyethylene glycol, polyols, saccharides, oligosaccharides, polypeptides, oligopeptides, and combinations thereof. The polypeptide may be any arrangement of amino acids ranging from about 100 to about 300,000 Daltons.

In one embodiment, a binder may be introduced into the mixture to be granulated in a solid form, for instance, as a crystal, a particle, a powder, or any other finely divided solid form known in the art. In another embodiment, the binder may be dissolved or suspended in a solvent and sprayed onto the mixture in a granulation device as a binder fluid during granulation.

A binder may be optionally present in a total amount of from about 0.01 wt % to about 15 wt %, for example from about 0.05 wt % to about 2 wt %, from about 0.1 wt % to about 2.5 wt %, or from about 0.1 wt % to about 0.5 wt %.

(xxiv) Diluents (Fillers)

An oral care composition of the invention may comprise a diluent (filler). Suitable diluents may include, without limit, carbohydrates, inorganic compounds, biocompatible polymers, e.g., polyvinylpyrrolidone (PVP), dibasic calcium sulfate, tribasic calcium sulfate, starch, calcium carbonate, magnesium carbonate, microcrystalline cellulose, dibasic calcium phosphate, tribasic calcium phosphate, magnesium carbonate, magnesium oxide, calcium silicate, talc, modified starches, saccharides such as sucrose, dextrose, lactose, microcrystalline cellulose, fructose, xylitol, and sorbitol, polyhydric alcohols, starches, pre-manufactured direct compression diluents, and mixtures thereof. A filler may be optionally present in a total amount of from about 0.01 wt % to about 15 wt %, for example from about 0.05 wt % to about 2 wt %, from about 0.1 wt % to about 2.5 wt %, or from about 0.1 wt % to about 0.5 wt %.

(xxv) Disintegrants

An oral care composition of the invention may comprise a disintegrant. Generally speaking disintegrants may be non-effervescent or effervescent. Suitable non-effervescent disintegrants may include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pectin, and tragacanth. Suitable effervescent disintegrants may include, without limit, sodium bicarbonate in combination with citric acid, and sodium bicarbonate in combination with tartaric acid. A disintegrant may be optionally present in a total amount of from about 0.01 wt % to about 15 wt %, for example from about 0.05 wt % to about 2 wt %, from about 0.1 wt % to about 2.5 wt %, or from about 0.1 wt % to about 0.5 wt %.

(xxvi) Preservatives

An oral care composition of the invention may comprise one or more preservatives. Suitable preservatives may include, without limit, ascorbic acid and its salts, ascorbyl palm itate, ascorbyl stearate, anoxomer, N-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), and polyphenol epigallocatechin-3-gallate, with the exception of EGCG), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palm ityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanillic acid, 2,6-di-tert-butyl-4-hydroxymethylphenol lonox 100), 2,4-(tris-3',5'-bi-tert-butyl-4'-hydroxybenzyl)-mesitylene (i.e., lonox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivatives thereof, vitamin Q10, wheat germ oil, zeaxanthin, or combinations thereof. In an exemplary embodiment, the preservative is an antioxidant, such as a-tocopherol or ascorbate, and antimicrobials, such as parabens, chlorobutanol or phenol.

A preservative may be optionally present in a total amount of from about 0.01 wt % to about 15 wt %, for example from about 0.05 wt % to about 2 wt %, from about 0.1 wt % to about 2.5 wt %, or from about 0.1 wt % to about 0.5 wt %.

(xxvii) Lubricants

An oral care composition may comprise a lubricant or glidant. Lubricants may be utilized to lubricate ingredients that form a pharmaceutical composition. As a glidant, the lubricant facilitates removal of solid dosage forms during the manufacturing process. Lubricants and glidants may include, without limit, magnesium stearate, calcium stearate, zinc stearate, hydrogenated vegetable oils (e.g., Sterotex®), polyoxyethylene monostearate, talc, polyethylene glycol, sodium benzoate, sodium lauryl sulfate, magnesium lauryl sulfate, and light mineral oil. The pharmaceutical composition will generally comprise from about 0.01 wt % to about 10 wt % of a lubricant. In some embodiments, the pharmaceutical composition will comprise from about 0.1 wt % to about 5 wt % of a lubricant. In a further embodiment, the pharmaceutical composition will comprise from about 0.5 wt % to about 2 wt % of a lubricant.

(xxviii) Dispersants

An oral care composition of the invention may include a dispersant. Suitable dispersants may include, without limitation, starch, alginic acid, polyvinylpyrrolidones, guar gum, kaolin, bentonite, purified wood cellulose, sodium starch glycolate, isoamorphous silicate, and microcrystalline cellulose as high hydrophilic-lipophilic balance (HLB) emulsifier surfactants. A dispersant may be optionally present in a total amount of from about 0.01 wt % to about 15 wt %, for example from about 0.05 wt % to about 2 wt %, from about 0.1 wt % to about 2.5 wt %, or from about 0.1 wt % to about 0.5 wt %.

(xxix) pH Modifers

An oral care composition of the invention may include one or more pH modifiers. Suitable pH modifiers may include, without limitation, citric acid, acetic acid, tartaric acid, malic acid, fumaric acid, lactic acid, phosphoric acid, sorbic acid, benzoic acid, sodium carbonate, and sodium bicarbonate. Any pH modifier included in the oral care composition should not impede the ability of the oral care composition to inhibit mutans streptococci. A pH modifier may be optionally present in a total amount of from about 0.01 wt % to about 15 wt %, for example from about 0.05 wt % to about 2 wt %, from about 0.1 wt % to about 2.5 wt %, or from about 0.1 wt % to about 0.5 wt %.

(xxx) Chelatinq Agents

An oral care composition of the invention may comprise a chelating agent. Suitable chelating agents may include, without limitation, lysine, methionine, glycine, gluconate, polysaccharides, glutamate, aspartate, and disodium ethylenediaminetetraacetate (Na2EDTA). A chelating agent may be optionally present in a total amount of from about 0.01 wt % to about 15 wt %, for example from about 0.05 wt % to about 2 wt %, from about 0.1 wt % to about 2.5 wt %, or from about 0.1 wt % to about 0.5 wt %.

(xxxi) Release-Controlling Polymers

An oral care composition of the invention may include one or more release-controlling polymers. Several classes of polymers suitable for the invention herein are known in the art, as disclosed by U.S. Pat. No. 6,197,346, the entire disclosure of which is hereby incorporated by reference. A release-controlling polymer may be optionally present in a total amount of from about 0.01 wt % to about 15 wt %, for example from about 0.05 wt % to about 2 wt %, from about 0.1 wt % to about 2.5 wt %, or from about 0.1 wt % to about 0.5 wt %.

II. METHODS OF TREATING MUTANS STREPTOCOCCI

An aspect of the present disclosure provides a method of treating mutans streptococci with an oral care composition of the invention comprising agmatine and EGCG, as detailed above. As used herein, the term "treating" refers to inhibiting the growth of, reducing the amount of, or abolishing the growth of mutans streptococci.

In general, a method of treating mutans streptococci involves administration of an oral care composition of the invention that contacts mutans streptococci in the oral cavity of a subject. In some embodiments, a method of treatment comprises administering an oral care composition of the invention to an oral cavity comprising S. mutans, S. sobrinus, or a combination thereof. S. sobrinus serotypes may be serotype d S. sobrinus, serotype g S. sobrinus, or serotypes d and g S. sobrinus. S. mutans serotypes may be serotype c S. mutans, serotype e S. mutans, serotype f S. mutans, serotypes c, e, and f S. mutans, or any combination of S. mutans serotypes selected from serotypes c, e, and f.

In some embodiments, the amount of colony forming units (cfu) of mutans streptococci treated with the oral care composition of the invention can and will vary depending on certain variables. Non limiting examples of such variables include, serotype(s) of mutans streptococci, strain(s) of mutans streptococci, the growth rate of mutans streptococci, and the environment sustaining the mutans streptococci, including factors such as the tonicity, pH, temperature, and other environmental factors known to impact mutans streptococci. In some embodiments, a method of treatment detailed herein may be directed to administering the oral care composition of the invention to mutans streptococci, wherein the amount of mutans streptococci is from about $1\times10^4$ cfu/ml to about $1\times10^7$ cfu/ml. In other embodiments, the method of treatment may be directed to administering the oral care composition of the invention to mutans streptococci, wherein the amount of mutans streptococci is at least about $1\times10^4$ cfu/ml, at least about $5\times10^4$ cfu/ml, at least about $1\times10^5$ cfu/ml, at least about $5\times10^5$ cfu/ml, at least about $1\times10^6$ cfu/ml, at least about $5\times10^5$ cfu/ml, or at least about $1\times10^7$ cfu/ml. For example, the amount of mutans streptococci can be at least about $2.0\times10^4$ cfu/ml, at least about $2.3\times10^4$ cfu/ml, at least about $2.5\times10^4$ cfu/ml, at least about $2.7\times10^4$ cfu/ml, at least about $2.9\times10^4$ cfu/ml, at least about $3.0\times10^4$ cfu/ml, at least about $2.3\times10^4$ cfu/ml, at least about $1.0\times10^5$ cfu/ml, at least about $1.1\times10^5$ cfu/ml, at least about $1.2\times10^5$ cfu/ml, at least about $1.3\times10^5$ cfu/ml, at least about $1.4\times10^5$ cfu/ml, at least about $1.0\times10^6$ cfu/ml, at least about $1.1\times10^6$ cfu/ml, at least about $1.2\times10^6$ cfu/ml, at least about $1.3\times10^6$ cfu/ml, at least about $1.4\times10^6$ cfu/ml, at least about $1.5\times10^6$ cfu/ml, at least about $5.0\times10^6$ cfu/ml, at least about $5.1\times10^6$ cfu/ml, at least about $5.2\times10^6$ cfu/ml, at least about $5.3\times10^6$ cfu/ml, or at least about $5.4\times10^6$ cfu/ml.

(i) Dosage

Generally speaking, an oral care composition of the invention is administered in a therapeutically effective amount. A therapeutically effective amount can and will vary depending on the subject, the formulation, severity of infection, or a combination therefore. In an embodiment, a therapeutically effective amount may be from about 1 µL to about 50 mL. In some embodiments, the therapeutically effective amount may be at least about 1 µL, at least about 2 µL, at least about 3 µL, at least about 4 µL, at least about 5 µL, at least about 6 µL, at least about 7 µL, at least about 8 µL, at least about 9 µL, at least about 10 µL, at least about 11 µL, at least about 12 µL, at least about 13 µL, at least about 14 µL, at least about 15 µL, at least about 16 µL, at least about 17 µL, at least about 18 µL, at least about 19 µL, at least about 20 µL, at least about 21 µL, at least about 22 µL, at least about 23 µL, at least about 24 µL, at least about 25 µL, at least about 26 µL, at least about 27 µL, at least about 28 µL, at least about 29 µL, at least about 30 µL, at least about 31 µL, at least about 32 µL, at least about 33 µL, at least about 34 µL, at least about 35 µL, at least about 36 µL, at least about 37 µL, at least about 38 µL, at least about 39 µL, at least about 40 µL, at least about 41 µL, at least about 42 µL, at least about 43 µL, at least about 44 µL, at least about 45 µL, at least about 46 µL, at least about 47 µL, at least about 48 µL, at least about 49 µL, at least about 50 µL, at least about 51 µL, at least about 52 µL, at least about 53 µL, at least about 54 µL, at least about 55 µL, at least about 56 µL, at least about 57 µL, at least about 58 µL, at least about 59 µL, at least about 60 µL, at least about 61 µL, at least about 62 µL, at least about 63 µL, at least about 64 µL, at least about 65 µL, at least about 66 µL, at least about 67 µL, at least about 68 µL, at least about 69 µL, at least about 70 µL, at least about 71 µL, at least about 72 µL, at least about 73 µL, at least about 74 µL, at least about 75 µL, at least about 76 µL, at least about 77 µL, at least about 78 µL, at least about 79 µL, at least about 80 µL, at least about 81 µL, at least about 82 µL, at least about 83 µL, at least about 84 µL, at least about 85 µL, at least about 86 µL, at least about 87 µL, at least about 88 µL, at least about 89 µL, at least about 90 µL, at least about 91 µL, at least about 92 µL, at least about 93 µL, at least about 94 µL, at least about 95 µL, at least about 96 µL, at least about 97 µL, at least about 98 µL, at least about 99 µL, at least about 1 mL, at least about 1.5 mL, at least about 2 mL, at least about 2.5 mL, at least about 3 mL, at least about 3.5 mL, at least about 4 mL, at least about 4.5 mL, at least about 5 mL, at least about 6 mL, at least about 7 mL, at least about 8 mL, at least about 9 mL, at least about 10 mL, at least about 11 mL, at least about 12 mL, at least about 13 mL, at least about 14 mL, at least about 15 mL, at least about 16 mL, at least about 17 mL, at least about 18 mL, at least about 19 mL, at least about 20 mL, at least about 21 mL, at least about 22 mL, at least about 23 mL, at least about 24 mL, at least about 25 mL, at least about 26 mL, at least about 27 mL, at least about 28 mL, at least about 29 mL, at least about 30 mL, at least about 31 mL, at least about 32 mL, at least about 33 mL, at least about 34 mL, at least about 35 mL, at least about 36 mL, at least about 37 mL, at least about 38 mL, at least about 39 mL, at least about 40 mL, at least about 41 mL, at least about 42 mL, at least about 43 mL, at least about 44 mL, at least about 45 mL, at least about 46 mL, at least about 47 mL, at least about 48 mL, at least about 49 mL, or at least about 50 m L.

(ii) Frequency

An oral care composition of the invention may be used to treat mutans streptococci with one or more than one administrations of the oral care composition. In some embodiments, an oral care composition of the invention is administered until all mutans streptococci are eradicated. In yet another embodiment, mutans streptococci may be treated with multiple administrations of an oral care composition of the invention until the growth of mutans streptococci is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% compared to levels before administration. In still another embodiment, mutans streptococci may be treated with multiple administrations of an oral care composition of the invention until the amount of mutans streptococci is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% compared to levels before administration.

In an embodiment, mutans streptococci may be treated with an oral care composition of the invention at least daily, twice daily, or three times daily. Administration may continue for 1, 2, 3, 4, 5, 6, 7, 8, 9, 10, 11, 12, 13, 14 or more than 14 days. For instance, administration may continue for 1, 2, 3, 4, 5, 6, 7, 8, 9, 10, 11, 12, 13, 14, 15, 16, 17, 18, 19, 20, 21, 22, 23, 24, or more than 24 weeks. In some embodiments, administration may continue for 1, 2, 3, 4, 5, 6, 7, 8, 9, 10, 11, 12, 13, 14, 15, 16, 17, 18, 19, 20, 21, 22, 23, 24, or more than 24 months.

In some embodiments, the additional administrations may be administered at least daily for at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 3 months, at least about 4 months, at least about 6 months, at least about 9 months, at least about 1 year, at least about 2 years, at least about 3 years, at least about 5 years, or at least about 10 years. In other embodiments, the additional administrations may be administered at least about every other day for at least about 3 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 3 months, at least about 4 months, at least about 6 months, at least about 9 months, at least about 1 year, at least about 2 years, at least about 3 years, at least about 5 years, or at least about 10 years. In still other embodiments, the additional administrations may be administered at least weekly for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 3 months, at least about 4 months, at least about 6 months, at least about 9 months, at least about 1 year, at least about 2 years, at least about 3 years, at least about 5 years, or at least about 10 years. In other embodiments, the additional administrations may be administered at least monthly for at least about 5 weeks, at least about 6 weeks, at least about 7 weeks, at least about 8 weeks, at least about 9 weeks, at least about 10 weeks, at least about 3 months, at least about 4 months, at least about 6 months, at least about 9 months, at least about 1 year, at least about 2 years, at least about 3 years, at least about 5 years, or at least about 10 years.

(iii) Subject

A suitable subject includes a human, a livestock animal, a companion animal, a lab animal, or a zoological animal. In one embodiment, the subject may be a rodent, e.g., a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a specific embodiment, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In preferred embodiments, the subject is a human.

III. METHODS OF TREATING CARIES

Another aspect of the present disclosure provides a method of treating dental caries with an oral care composition of the invention comprising agmatine and EGCG, as detailed above. As used herein, the term "treating" refers to reducing the size of dental caries in a subject, preventing dental caries in a subject, reducing the incidence of dental caries in a subject, or eliminating dental caries in a subject. The method comprises administering an oral care composition to a subject, as detailed above.

IV. DEFINITIONS

The term "prodrug," as used herein refers to a compound which is administered in an inactive (or less active) form that is metabolized in vivo into an active (or more active) form.

The term "analog" as used herein refers to a compound that is similar or comparable, but not identical, to a reference compound, i.e. a compound similar in function and appearance, but not in structure or origin to the reference compound. For example, the reference compound may be EGCG and an analog is a substance possessing a chemical structure or chemical properties similar to those of EGCG. As used herein, an analog is a chemical compound that may be structurally similar to another but differs in composition (as in the replacement of one atom by an atom of a different element or in the presence of a particular functional group). An analog may be extracted from a natural source or be prepared using synthetic methods.

As used herein, an "effective amount" of a compound and/or composition used for any in vivo or in vitro application will depend upon a variety of factors including, but not limited to, the activity of the specific compound employed, time of administration, route of administration, drug combination, the severity of oral colonization by mutans streptococci, the severity of dental caries, or the age, body weight, general health, sex, and/or diet of the subject.

By "pharmaceutically-acceptable excipient" or "pharmaceutically-acceptable carrier," as used herein, is meant one or more compatible solid or liquid filler diluents or encapsulating substances which are suitable for topical, oral administration. By "compatible," as used herein, is meant that the components of the oral care composition are capable of being commingled without interaction in a manner which would substantially reduce the oral care composition's stability and/or efficacy for treating or preventing breath malodor, plaque, gingivitis, periodontal disease and to whiten the teeth, according to the oral care compositions and methods of the present invention.

When introducing elements herein, the articles "a", "an", "the" and "said" are intended to mean that there are one or more of the elements. The terms "comprising", "including" and "having" are intended to be inclusive and mean that there may be additional.

As various changes could be made in the above compositions and methods without departing from the scope of the invention, it is intended that all matter contained in the above description shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Preparation of a Toothpaste Formulation

A prototype toothpaste gel formulation useful in the present invention was prepared, but is not limited to, the following components (TABLE 1):

TABLE 1

| Toothpaste Gel Formulation | |
| --- | --- |
| Ingredient | Quantity |
| Agmatine | 3.7878 g |
| EGCG/Potassium Sorbate Triturate Stock | 6.519 g |
| Saccharin Sodium, USP (dehydrate) | 1.50 g |
| Glycerin, USP | 37.5 ml |
| Sorbitol Solution, USP 70% (w/w) | 75.0 ml |
| Simethicone, USP | 3.75 ml |
| Carbomer 934P, NF | 9.00 g |
| Trolamine, NF liquid | 7.50 ml |
| Preserved-Parabens Water | q.s. 757.50 ml |

Prior to preparing the toothpaste gel formulation, an EGCG/potassium sorbate triturate stock was prepared. EGCG (0.038 g) and potassium sorbate (3.010 g) were combined and reduced to a fine powder in a mortar. The resulting triturate was combined with diluent (preserved-parabens water) by geometric dilution and stored for later use.

To prepare the toothpaste gel formulation, glycerin, sorbitol solution, and simethicone were mixed in a beaker containing preserved water (q.s. 50% of final volume). Carbomer 934P was then added and the components were slowly mixed with a mixing drill and an unguator mixing blade until a gel was formed. Once the gel was formed, the beaker was covered, and allowed to stand for at least 3 hours to disperse any bubbles that were formed in the mixing process. In a separate beaker, agmatine, EGCG/potassium sorbate triturate stock, and saccharin sodium were dissolved in preserved water (q.s. 32% of final volume) to yield a "milky liquid", free of solid material and/or precipitates. The milky liquid was added to gel in addition to preserved water (q.s. 99% of final volume). Finally, trolamine was added, and the combined components were gently mixed with a spatula until fully uniform. The resulting toothpaste gel formulation was packaged into tubes by standard methods known in the art.

Example 2. Agmatine and EGCG in Combination Synergistically Kill Streptococcus mutans Because the primary bacterium responsible for dental caries (cavities) is *Streptococcus mutans*, the killing efficacy of agmatine and EGCG, alone and in combination, was determined against *Streptococcus mutans*. Killing efficacy was measured in vitro using *Streptococcus mutans* cells grown in brain heart infusion (BHI) plates for at least 24-48 hours at 37° C. Each experiment was initiated by collecting an individual colony from the BHI plate and growning the colony overnight at 37° C. and 5% $CO_2$ in BHI liquid media. *Streptococcus mutans* cells were then passaged 2 times in chemically defined media for *Streptococcus mutans* and grown overnight at 37° C. and 5% $CO_2$. The absorbance at A600 of the culture was measured to determine the bacterial cell concentration of the inoculum. Once the desired bacterial cell concentration was reached, *Streptococcus mutans* inoculum was plated on cell culture plates previously prepared with a range of concentrations of EGCG alone, agmatine alone, or EGCG and agmatine in combination. The plates streaked with inoculum were incubated for at least 24 hours at 37° C. and 5% $CO_2$. After incubation, the cells were transferred to sterile tubes, plated on BHI plate using an Autoplate 4000, and incubated for at least 36 hours at 37° C. Colonies were counted and colony forming units (cfu) were calculated as recommended by Autoplate 4000 guide.

Data provided in FIGS. 1 to 4 was generated as follows: *Streptococcus mutans* inoculum ($2.71 \times 10^4$ cfu/ml) was plated on plates containing 6.255 µg/ml, 12.5 µg/ml, 25 µg/ml, 50 µg/ml, 100 µg/ml, or 200 µg/ml EGCG, 1.25 mg/ml, 2.5 mg/ml, 5 mg/ml, 7.5 mg/ml, or 10 mg/ml agmatine, or EGCG/agmatine at 3.125 µg/ml/0.6125 mg/ml, 6.25 µg/ml/1.25 mg/ml, 12.5 µg/ml/2.5 mg/ml, or 25 µg/ml/5 mg/ml. The plates were incubated overnight and remaining cells collected to measure *Streptococcus mutans* cell count following EGCG, agmatine, or EGCG/agmatine treatment.

Figure 4:
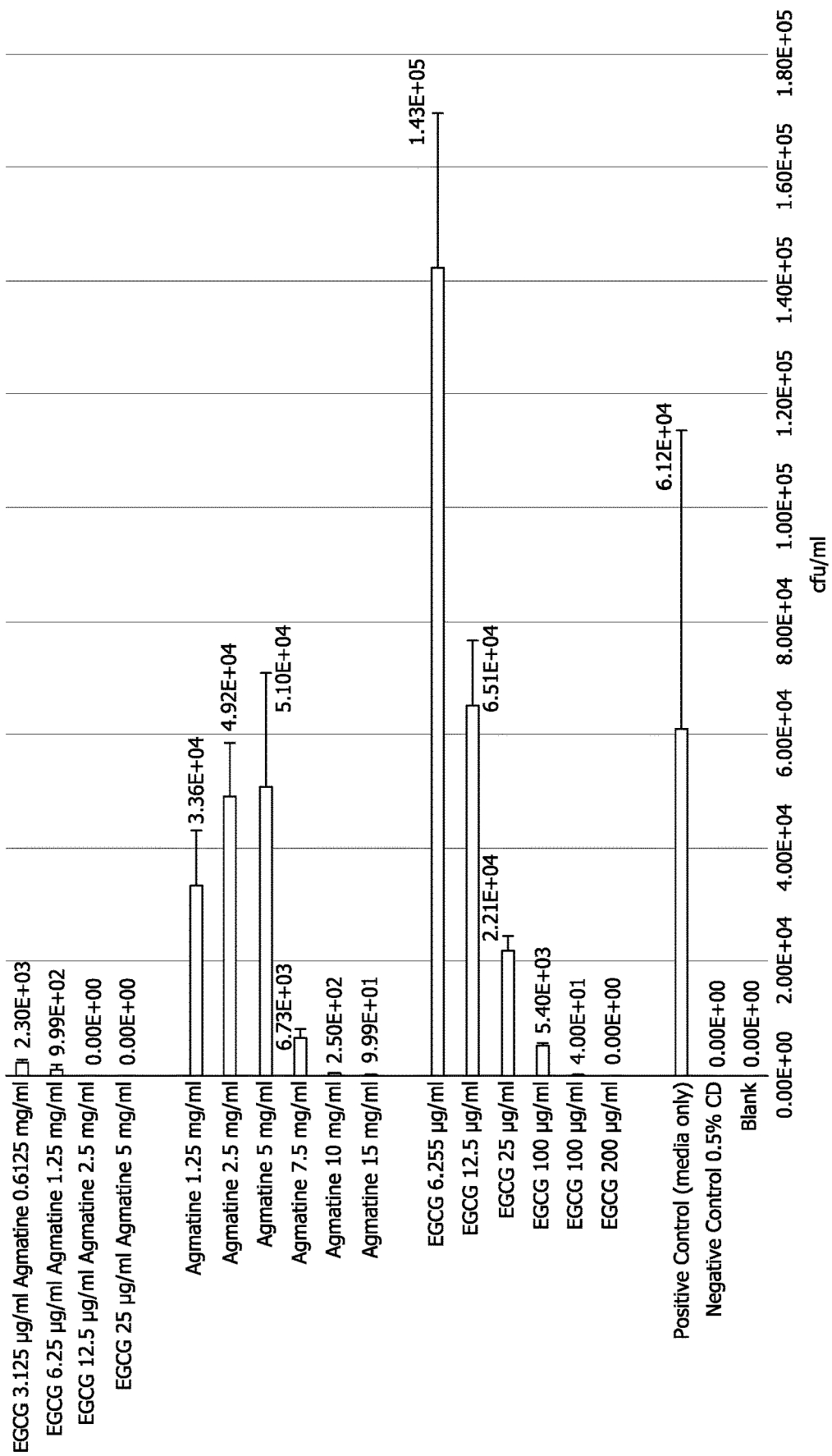
FIG. 4 depicts a graph showing the killing effect of EGCG, agmatine, or EGCG and agmatine in combination on *Streptococcus mutans* inoculum at $5.24 \times 10^6$ cfu/ml.

FIG. 1 shows that *Streptococcus mutans* inoculum ($2.71 \times 10^4$ cfu/ml) was completely killed ($0.00 \times 10^0$ cfu/ml) when treated with either 200 µg/ml EGCG or 10 mg/ml agmatine. However, when used in combination, *Streptococcus mutans* were completely killed by using only 25 µg/ml EGCG and 5 mg/ml agmatine. This synergy of EGCG and agmatine is also observed at other combinations with significant killing efficiencies. For example, the bacterial concentration of *Streptococcus mutans* inoculum following treatment with 50 µg/ml EGCG is $6.00 \times 10^1$ cfu/ml and treatment with 7.5 mg/ml agmatine is $6.50 \times 10^1$ cfu/ml, whereas the combined treatment of 12.5 µg/ml EGCG and 2.5 mg/ml agmatine has an equivalent killing efficiency ($6.50 \times 10^1$ cfu/ml) (FIG. 1). Further, the combination of EGCG and agmatine exhibits synergy across a range of *Streptococcus mutans* concentrations, specifically *Streptococcus mutans* inoculum at $1.38 \times 10^6$ cfu/ml (FIG. 2), *Streptococcus mutans* inoculum at $1.26 \times 10^5$ cfu/ml (FIG. 3), and *Streptococcus mutans* inoculum at $5.24 \times 10^6$ cfu/ml (FIG. 4).

What is claimed is:

1. A method of treating mutans streptococci in an oral cavity of a subject, the method comprising contacting mutans streptococci with an oral care composition, wherein the oral care composition comprises agmatine and EGCG in synergistic amounts effective to treat mutans streptococci in the oral cavity of the subject.

2. The method of claim 1, wherein the oral care composition comprises agmatine in an amount of about 0.6 mg/ml to about 5 mg/ml.

3. The method of claim 1, wherein the oral care composition comprises EGCG in an amount of about 3 µg/ml to about 25 µg/ml.

4. The method of claim 1, wherein the mutans streptococci comprise at least one serotype of *Streptococcus mutans*.

5. The method of claim 1, wherein the oral care composition is formulated with a pharmaceutically acceptable carrier.

6. The method of claim 1, wherein the oral care composition is alcohol-free.

7. The method of claim 1, wherein the oral care composition is formulated as a dentifrice, a toothpaste, a tooth gel, a dental cream, a mouthwash, a mouthrinse, a lozenge, a mousse, a foam, a mouth spray, an oral tablet, a dental implement, a chewing gum, a mint, chew, drink power, concentrated drink mix, liquid drink, or tea.

8. The method of claim 1, wherein treating mutans streptococci comprises inhibiting the growth of mutans streptococci, reducing the amount of mutans streptococci, or abolishing the growth of mutans streptococci.

9. A method of treating caries in a subject, the method comprising administering an oral care composition, wherein the oral care composition comprises agmatine and EGCG in synergistic amounts effective to treat caries in the subject.

10. The method of claim 9, wherein the oral care composition comprises agmatine in an amount of from about 0.6 mg/ml to about 5 mg/ml.

11. The method of claim 9, wherein the oral care composition comprises EGCG in an amount of about 3 µg/ml to about 25 µg/ml.

12. The method of claim 8, wherein the oral care composition is formulated with a pharmaceutically acceptable carrier.

13. The method of claim 9, wherein the oral care composition is formulated as a dentifrice, a toothpaste, a tooth gel, a dental cream, a mouthwash, a mouthrinse, a lozenge, a mousse, a foam, a mouth spray, an oral tablet, a dental implement, a chewing gum, a mint, chew, drink powder, concentrated drink mix, liquid drink, or tea.

14. An oral care composition, the oral care composition comprising agmatine and EGCG in synergistic amounts effective to inhibit the growth of, reduce the amount of, or abolish the growth of mutans streptococci.

15. The oral care composition of claim 14, wherein the oral care composition comprises agmatine in an amount of about 0.6 mg/ml to about 5 mg/ml.

16. The oral care composition of claim 14, wherein the oral care composition comprises EGCG in an amount of about 3 µg/ml to about 25 µg/ml.

17. The oral care composition of claim 14, wherein the mutans streptococci comprise at least one serotype of *Streptococcus mutans*.

18. The oral care composition of claim 14, wherein the oral care composition is formulated with a pharmaceutically acceptable carrier.

19. The oral care composition of claim 14, wherein the oral care composition is formulated as a dentifrice, a toothpaste, a tooth gel, a dental cream, a mouthwash, a mouthrinse, a lozenge, a mousse, a foam, a mouth spray, an oral tablet, a dental implement, a chewing gum, a mint, chew, drink powder, concentrated drink mix, liquid drink, or tea.

20. The oral care composition of claim 14, wherein the oral care composition further comprises a component selected from the group consisting of an additional antimicrobial agent, an anti-plaque agent, a tooth whitening or tooth bleaching composition, a flavorant, a sweetening agent, an adhesion agent, a surfactant, a foam modulator, an abrasive, a humectant, a mouth feel agent, a colorant, a tartar control agent, a fluoride ion source, a saliva stimulating agent, a thickening agent, an anti-sensitivity agent, an antioxidant, a nutrient, an enzyme, a propellant, a binder, a diluent, a disintegrant, a preservative, a lubricant, a dispersant, a pH modifier, a chelating agent, a release-controlling polymer, and a combination thereof.

* * * * *